United States Patent [19]

Urban et al.

[11] Patent Number: 5,389,328
[45] Date of Patent: Feb. 14, 1995

[54] PROCESS FOR THE FABRICATION OF ORTHOPAEDIC AIDS BASED ON EPOXY RESINS AND POLYAMINES

[75] Inventors: Klaus D. Urban; Hans R. Felzl, both of Vienna, Austria

[73] Assignee: Ciba-Geigy Corporation, Ardsley, N.Y.

[21] Appl. No.: 23,036

[22] Filed: Feb. 24, 1993

[30] Foreign Application Priority Data

Feb. 28, 1992 [CH] Switzerland ............................ 621/92

[51] Int. Cl.⁶ ...................... B29C 43/00; B29C 51/00
[52] U.S. Cl. .................................... 264/294; 264/322; 264/325
[58] Field of Search ................... 264/16, 17, 222, 220, 264/219, 294, DIG. 30, 319, 320, 322, 325; 425/2; 602/7, 8

[56] References Cited

U.S. PATENT DOCUMENTS

| | | | |
|---|---|---|---|
| Re. 30,541 | 3/1981 | Larson | 602/7 |
| 3,307,537 | 3/1967 | Simon et al. | 602/8 |
| 3,517,091 | 6/1970 | Ellman | 264/16 |
| 3,692,023 | 9/1972 | Phillips et al. | 602/7 |
| 3,708,567 | 1/1973 | Hampel | 264/331 |
| 3,906,943 | 9/1975 | Arluck | 602/7 |
| 4,530,352 | 7/1985 | Holloway | 602/8 |
| 4,704,129 | 11/1987 | Massey | 264/222 |
| 4,874,833 | 10/1989 | Kershaw | 528/90 |

FOREIGN PATENT DOCUMENTS

| | | |
|---|---|---|
| 0355924 | 2/1990 | European Pat. Off. . |
| 1270267 | 6/1968 | Germany . |
| 2238285 | 12/1982 | Germany . |
| 1169121 | 10/1969 | United Kingdom . |
| 1371967 | 10/1974 | United Kingdom . |

OTHER PUBLICATIONS

Kunststoff-Handliuch, Band XI, Polyacetale Epoxidharze, fluorhaltige Polymerisate, Silicon USW (1971).
Lee & Neville, "Handbook of Epoxy Resins," McGraw-Hill, Inc., N.Y. 1967, Chapter 2.
Lee & Neville, "Handbook of Epoxy Resins", McGraw-Hill, Inc., N.Y. 1967 Chapters 7 & 8.

*Primary Examiner*—Mathieu D. Vargot
*Attorney, Agent, or Firm*—William A. Teoli, Jr.

[57] ABSTRACT

A process is provided for the fabrication of orthopaedic aids from a semifinished material which is obtainable from a hardened material based on one or more than one epoxy resin and one or more than one polyamine as essential polymer component, which process includes shaping the hardened material after heating said material to above the glass transition point and cooling it again, to the use of said material for the fabrication of made-to-measure orthopaedic aids and to the orthopaedic aids so obtained.

8 Claims, No Drawings

PROCESS FOR THE FABRICATION OF ORTHOPAEDIC AIDS BASED ON EPOXY RESINS AND POLYAMINES

TECHNICAL FIELD

A process is provided for the fabrication of orthopaedic aids, to the use of hardened material obtainable from formulations based on epoxy resins and polyamines as essential polymer components, to the fabrication of orthopaedic aids and to the orthopaedic aids so obtained.

BACKGROUND

Orthopaedic aids such as shoe inserts or corsets, typically for spinal correction in treating wrong posture, usually have to be shaped to a very specific form which is individually accommodated to a specific wearer.

To enable this accommodation to be made in simple manner, such orthopaedic aids have for some time been increasingly made from polymethacrylate (PMMA), i.e. a thermoplastic polymer. The procedure normally comprises first mechanically preforming a semifinished product made from the material, typically a polyamethacrylate board, by customary mechanical shaping methods such as cutting, milling, drilling, abrading or polishing. The final shaping, i.e. the exact matching of the blank so obtained to the requirements of a specific patient, is finally performed by thermoforming, i.e. by a shaping operation in which the material is heated so that it becomes elastic.

Polymethylmethacrylate has, however, a number of shortcomings in the above described process, which make it desirable to find a substitute material. On the one hand, PMMA begins to soften at quite low temperatures, so that mechanical processing can only be carried out with difficulty, as the tools easily become tacky or the material becomes soft and stringy. On the other hand, rather high temperatures of c. 180° C. are required for the final thermoforming, as only after shaping at such high temperatures is a sufficiently low, degree of elastic memory ensured. Aside from the time and effort involved, the danger of hydrocyanic acid emission is always present when heating plexiglass material to such high temperatures.

SUMMARY

It is therefore the object of this invention to provide a material for use as semifinished material for fabricating made-to-measure orthopaedic aids that does not have the shortcomings of PMMA, and a process for the fabrication of said orthopaedic aids.

It has now been found that hardened material obtainable from a formulation based on one or more than one epoxy resin and one or more than one polyamine as essential polymer component is a suitable material for the fabrication of made-to-measure orthopaedic aids like those mentioned above. It is particularly surprising that amine-cured epoxy resin material, which in contrast to the thermopolastic polymer PMMA is a thermosetting polymer, can be heat-formed on the dimensionally large scale that is normally necessary for the fabrication of orthopaedic aids.

A further object of the invention is therefore the use of cured material obtainable from a formulation based on one or more than one epoxy resin and one or more than one polyamine as essential polymer component for the fabrication of made-to-measure orthopaedic aids.

It is yet a further object of the invention to provide a process for the fabrication of orthopaedic aids made from semifinished material that is obtainable from a formulation based on one or more than one epoxy resin and one or more than one polyamine as main polymer component, which comprises shaping the hardened material after heating said material above the glass transition point and cooling it again.

The epoxy resins for the preparation of the hardened material are preferably selected from cycloaliphatic epoxy resins, epoxy resins based on 2,2-bis(4-hydroxyphenyl)propane (bisphenol A), bis(4-hydroxyphenyl)methane (bisphenol F) or on novolaks, i.e. phenol/formaldehyde condensates obtained under acid conditions. Epoxy resins of this kind are commonly known and are described, inter alia, in LEE & NEVILLE "Handbook of Epoxy Resins", McGraw-Hill, Inc., New York, 1967, Chapter 2. Such epoxy resins are also commercially available in diverse forms.

DETAILED DESCRIPTION

Particularly preferred epoxy resins are diglyicdyl or polyglycidyl ethers and di- or poly($\beta$-methylglycidyl) ethers of bisphenol A and of phenol and cresol-novolaks. These compounds can also be very readily used in admixture.

It is also preferred to use a material in which the polyamines are selected from aromatic polyamines, cycloaliphatic polyamines and aliphatic and heteroaliphatic polyamines. By "heteroaliphatic amines" are meant in this context amines that contain the hetero atoms in the aliphatic chain, typically polyether polyamines. Particularly suitable polyamines are those containing primary amino groups. Suitable polyamines of this type are also generally known. A survey of amines of this type will be found in LEE & NEVILLE "Handbook of Epoxy Resins", McGraw-Hill, Inc., New York, 1967, Chapters 7 and 8. Many polyamines of the above type suitable for use in the practice of this invention are also commercially available.

Epoxy resins and amines are used in customary ratios for preparing the curable material eligible for use in the practice of this invention, i.e. quite generally in approximately equivalent amounts, typically in amounts of 0.8 to 1.5, preferably of 1 to 1.3, equivalents of active hydrogen bonded to amino nitrogen atoms per 1 epoxide equivalent.

It has been found especially useful if the eligible material contains flexibilising components. The flexibilisation can be achieved by using epoxy resins and/or polyamines which are modified by incorporating non-rigid molecular groups between the functional groups used for crosslinking, conveniently long chains of atoms or groups of atoms that are linked by means of single bonds. The chain length of the flexibilising groups should in this case be preferably 8 and more atoms or groups of atoms. In addition, it is possible to use monofunctional groups that contain an appropriate flexibilising molecular group, typically monoamines of suitable structure.

A particularly preferred embodiment of the invention comprises the use of a hardened material in which the polyamines are selected from cycloaliphatic polyamines as well as from aliphatic and heteroaliphatic polyamines, the aliphatic and heteroaliphatic polyamines containing at least one amino group separated by 8 or more atoms from the nearest amino group.

Suitable cycloaliphatic polyamines are preferably derivatives of cyclohexane, typically diaminocyclohexane or bis(4-aminocyclohexyl)methane and similar compounds which may also be substituted, preferably by $C_1$-$C_4$alkyl, for example bis(3-methyl-4-aminocyclohexyl)methane. Also very suitable are amines of the general formula R-NH-$(CH_2)_x$-$(CHR^1)_y$-$(CH_2)_z$-$NH_2$, wherein R is a cycloalkyl group, preferably of 1 to 10 carbon atoms, or a cycloalkylalkyl group, preferably of 1 to 20 carbon atoms and both types of groups may also carry one or more than one halogen, $C_1$-$C_{10}$alkyl or aryl substituent, and $R^1$ is a $C_1$-$C_{10}$alkyl group, the indices x and z are each independently of the other an integer from 0 to 10 and y is 0 or 1, but x, y and z may never all simultaneously be 0. Exemplary of a compound of this type is 1-(N-hexahydrobenzyl-amino)-3-aminopropane. The amino compounds cited herein have already been used for epoxy resin materials for making spectacle frames and are disclosed, inter alia, in GB patent 1 169 121. A very particularly preferred cycloaliphatic polyamine is 3-(aminomethyl)-3,5,5-trimethylcyclohexylamine (isophoronediamine).

Typical examples of aliphatic or heteroaliphatic polyamines carrying at least one amino group which is separated by 8 or more atoms from the nearest amino group are 1,8-diaminooctane, 1,10-diaminodecane or 1,12-diaminododecane. These and similar diamines can be readily obtained from the corresponding dinitriles, which can in turn be obtained by dehydration of corresponding acid amides. To this end the dinitriles are hydrogenated under pressure in an autoclave with liquid ammonia (4–8 mol per mol of dinitrile) and/or using methanol as solvent and Raney nickel as catalyst in the temperature range of up to c. 125° C. Further examples of polyamines of this type are polyoxyalkylene polyamines, typically the polyoxypropylene polyamines commercially available under the registered trademark of Jeffamines ®. A very particularly preferred polyether polyamine is dioxadodecanediamine, a known compound which is likewise commercially available.

It can also be expedient to prereact a primary polyamine initially with an epoxy resin to give a linear adduct and to use said adduct as hardener in the preparation of the eligible material. Such an adduct is preferably prepared at elevated temperature, e.g. at 80° to 200° C.

The inventive use of a material which is obtainable from one or more than one epoxy resin and a mixture of cycloaliphatic polyamines and aliphatic or heteroaliphatic polyamines as main polymer component, which aliphatic or heteroaliphatic polyamines carry at least one amino group which is separated by 8 or more atoms from the nearest amino group, has been found especially useful. The aliphatic or heteroaliphatic polyamines are preferably used in a weight ratio of 1:1 to 10:1 to each other. It is especially useful if the polyamine mixture consists of isophoronediamine and dioxadodecanediamine. The ratio of dioxadodecanediamine to isophoronediamine is conveniently 1:1 to 5:1, likewise based on weight, preferably 2:1 to 4:1.

The formulations from which the materials eligible for use in the practice of this invention are obtainable will often conveniently comprise, in addition to the epoxy resins and polyamines, conventional modifiers, preferably pigments, dyes, processing auxiliaries, accelerators as well as fillers and reinforcing agents.

The methods conventionally used in the epoxy art are suitable for preparing the amine-cured epoxy resin material, typically free casting, injection moulding, laminating, sheet moulding or pressure gelation. It is preferred to subject the material for some time, typically for 30 minutes to several hours, to an afterbake at 100°–150° C. The material can be stored and sold in this form and used as required as semifinished material for the fabrication of orthopaedic aids. The semifinished material is conveniently in the form of boards having a thickness of 2 to 10 mm. It may naturally also be often expedient to produce the semifinished material in a preformed state that is already accommodated to a specific shaping.

When fabricating orthopaedic aids from the semifinished material, a thermoforming to produce the final intended shape of the orthopaedic aid is additionally carried out. This is done by heating the hardened material first to a temperature above the glass transition point, normally in the temperature range from 80° to 150° C., preferably from 100° to 120° C., i.e. at substantially lower temperatures than are needed for thermoforming PMMA material. Suitable heat sources are heating cabinets, infrared radiators, hot air, gas flames or hot liquids such as oils, molten fats or, in suitable cases, also water. Afterwards the material is shaped in any desired manner, typically by hand or using a template or another special moulding tool, conveniently a press, and -set in the desired form- cooled again to a temperature below the glass transition point of the material. Cooling can be accelerated, if desired, by means of cold compressed air or cold water. When cooling to below the glass transition temperature, the cured and shaped material is conveniently set in the chosen shape.

In addition to the above described thermoforming, it may also be necessary or expedient to use mechanical shaping methods such as cutting, milling, drilling, polishing and the like. In contrast to thermoplastic materials, especially to PMMA, there is no danger of a premature softening of the cured epoxy material eligible for use in the practice of this invention with the negative consequences discussed at the outset.

Finally, the invention also relates to the orthopaedic aids which are at least partially accommodated by thermoforming to a predetermined shape and which are obtained from the hardened material of the above described type.

EXAMPLE

Example: 100 g of a epoxy resin based on bisphenol A having a molecular weight of less than 700 and an epoxy equivalent of 180–190 g/eq (ARALDIT ®GY 260) are mixed with 56 g of a hardener which is an adduct of 36 parts by weight of the same resin, 47 parts by weight of dioxadodecanediamine and 17 parts by weight of isophoronediamine (VESTAMIN ®IPD). The mixture is degassed at room temperature and a pressure of c. 1330 Pa for two hours. The degassed mixture is processed by pressure gelation for 5 minutes at 120° C. to c. 5 mm boards. The boards are then subjected to an afterbake for 1 hour at 120° C.

Blanks are cut from this semifinished material and compressed to a three-dimensional shape at c. 120° C. and up to c. 4 bar overpressure. After cooling in the press to room temperature, the material is removed from the mould and retains its shape.

What is claimed is:

1. A process for the fabrication of orthopaedic aids made from semifinished material that is obtainable from a cured material based on one or more than one epoxy resin and one or more than one polyamine as essential polymer component, which hardened material has a glass transition point, which process comprises: (i) heating said material to above the glass transition point; (ii) shaping the cured material to produce the intended shape of the orthopaedic aid; and (iii) cooling the shaped material to a temperature below the glass transition point.

2. A process according to claim 1, wherein the epoxy resins are selected from the group consisting of cycloaliphatic epoxy resins, epoxy resins based on bisphenol A, epoxy resins based on bisphenol F and epoxy resins based on novolaks.

3. A process according to claim 1, wherein the polyamines are selected from the group consisting of aromatic polyamines, cycloaliphatic polyamines, aliphatic polyamines and heteroaliphatic polyamines.

4. A process according to claim 3, wherein the polyamines are selected from the group consisting of cycloaliphatic polyamines, aliphatic polyamines and heteroaliphatic polyamines, wherein the aliphatic polyamines and heteroaliphatic polyamines contain at least one amino group separated by 8 or more atoms from the nearest amino group.

5. A process according to claim 4, wherein the hardened material is obtainable from one or more than one epoxy resin and a mixture of polyamines selected from the group consisting of cycloaliphatic polyamines, aliphatic polyamines and heteroaliphatic polyamines, wherein the aliphatic polyamines and heteroaliphatic polyamines contain at least one amino group separated by 8 or more atoms from the nearest amino group.

6. A process according to claim 5, wherein the mixture of polyamines consists of isophoronediamine and dioxadodecanediamine.

7. A process according to claim 1, wherein the hardened material is obtainable from a formulation that, in addition to comprising the epoxy resins and polyamines, further comprises as modifier a pigment, dye, processing auxiliary, accelerator, filler or reinforcing agent.

8. A process according to claim 1, wherein the semifinished material is additionally subjected to a mechanical shaping.

* * * * *